United States Patent [19]

Shin et al.

[11] Patent Number: 4,774,079

[45] Date of Patent: Sep. 27, 1988

[54] ANTIPERSPIRANT COMPOSITION CONTAINING ALUMINUM CHLOROHYDRATE, ALUMINUM CHLORIDE AND AN ALUMINUM ZIRCONIUM POLYCHLOROHYDRATE COMPLEX AND METHOD OF USE

[75] Inventors: Chung T. Shin, Livingston; Milton S. Slade, Maplewood; Ara Nersesian, Livingston, all of N.J.

[73] Assignee: Bristol-Myers Company, New York, N.Y.

[21] Appl. No.: 782,173

[22] Filed: Sep. 26, 1985

Related U.S. Application Data

[63] Continuation of Ser. No. 464,268, Feb. 7, 1983, abandoned, which is a continuation of Ser. No. 216,413, Dec. 15, 1980, abandoned.

[51] Int. Cl.$^4$ .......................... A61K 7/32; A61K 7/34; A61K 7/36; A61K 7/38
[52] U.S. Cl. .............................. 424/66; 424/DIG. 5; 424/67; 424/68; 424/69
[58] Field of Search ................................ 424/66, 68

[56] References Cited

U.S. PATENT DOCUMENTS

| | | | |
|---|---|---|---|
| 2,906,663 | 9/1959 | Beekman | 167/90 |
| 3,903,258 | 9/1975 | Siegal | 424/66 |
| 3,981,986 | 9/1976 | Rubino | 424/47 |
| 3,998,788 | 12/1976 | Rubino | 424/47 |
| 4,017,599 | 4/1977 | Rubino | 424/47 |
| 4,021,536 | 5/1977 | Rubino | 424/66 X |
| 4,025,615 | 5/1977 | Rubino | 424/66 |
| 4,028,390 | 6/1977 | Rubino | 260/429.3 |
| 4,049,792 | 9/1977 | Elsnau | 424/66 |
| 4,083,956 | 4/1978 | Shelton | 424/66 |
| 4,202,879 | 5/1980 | Shelton | 424/66 |

FOREIGN PATENT DOCUMENTS

| | | | |
|---|---|---|---|
| 2278319 | 7/1975 | France . | |
| 770008 | 3/1957 | United Kingdom | 424/66 |
| 835385 | 5/1960 | United Kingdom | 424/66 |
| 1353916 | 5/1974 | United Kingdom | 424/47 |
| 1353915 | 5/1974 | United Kingdom | 424/47 |
| 1353914 | 5/1974 | United Kingdom | 424/68 |
| 1453202 | 10/1976 | United Kingdom | 424/68 |
| 1487189 | 9/1977 | United Kingdom | 424/66 |
| 1515377 | 6/1978 | United Kingdom | 424/66 |
| 1549617 | 8/1979 | United Kingdom | 424/66 |
| 2076289 | 12/1981 | United Kingdom | 424/68 |

*Primary Examiner*—Dale R. Ore
*Attorney, Agent, or Firm*—Sandra M. Person

[57] ABSTRACT

An antiperspirant composition buffered to a pH in the range of from about 2.5 to about 4.5 having incorporated therein as active ingredients a combination of aluminum chlorohydrate, aluminum chloride and an aluminum zirconium polychlorohydrate complex; an additionally added buffering agent, preferably glycine, may be incorporated in the composition.

12 Claims, No Drawings

ANTIPERSPIRANT COMPOSITION CONTAINING ALUMINUM CHLOROHYDRATE, ALUMINUM CHLORIDE AND AN ALUMINUM ZIRCONIUM POLYCHLOROHYDRATE COMPLEX AND METHOD OF USE

This is a continuing application of application Ser. No. 464,268 filed on Feb. 7, 1983, which is a continuation of application Ser. No. 216,413, filed Dec. 15, 1980, both now abandoned.

This invention relates to antiperspirant compositions. More particularly, it concerns antiperspirant compositions having incorporated therein aluminum chlorohydrate, aluminum chloride, an aluminum zirconium polychlorohydrate complex and a buffering agent e.g. glycine.

Aluminum chlorhydrate (ACH) has been known for many years to be an effective and safe antiperspirant. Nevertheless, there is room for improvement and the search to find more effective antiperspirant materials is constantly going on. It has also been known in the art for sometime that aluminum chloride and zirconium salts provide exceptionally effective antiperspirants. However, solutions of aluminum chloride hexahydrate and zirconium oxy- or hydroxychloride are very acidic and therefore, they are not widely used alone because of their irritation potential and high fabric damage. Therefore, various efforts have been centered on raising the pH to 3 to 4 by using less acidic aluminum salts and incorporating organic nitrogen containing compounds.

Daley (U.S. Pat. Nos. 2,814,584 and 2,814,585) and Grad (U.S. Pat. No. 2,854,382) showed that when zirconium oxy- or zirconium hydroxychloride are buffered with ACH and glycine, the antiperspirant efficacy is greater than an ACH system alone. Since then, the combination of aluminum chlorohydrate, zirconium hydroxychloride and glycine has been used widely as a most effective antiperspirant active system.

Luedders et al in U.S. Pat. No. 3,792,068 suggest a process for preparing an antiperspirant which comprises spray drying a solution containing, for example, ACH, zirconyl hydroxychloride and glycine. It is claimed that this combination has superior characteristics not possessed when the components are dried separately and combined by simple physical mixing.

The British patent to Shin et al No. 1,347,950 discloses the use of a combination of ACH and aluminum chloride as an effective antiperspirant material. This combination was found to be particularly useful in an aerosol composition. However, as in the case with other antiperspirant materials known in the prior art, it still left room for improvement.

Other antiperspirant systems containing aluminum and zirconium salts have been reported, for example, Beekman (U.S. Pat. No. 2,906,668), Rubino (U.S. Pat. Nos. 3,979,510; 3,981,896 and 4,017,599), Siegel et al (U.S. Pat. No. 3,407,254), Mecca (U.S. Pat. No. 3,970,748), Shelton (U.S. Pat. No. 4,202,879), etc. The antiperspirant activity of all these salts in these patents has not been clearly claimed as having superiority over systems containing zirconium hydroxychloride, ACH and glycine.

Although aluminum chloride, aluminum chlorohydrate, zirconyl hydroxychloride and certain aluminum zirconium chlorohydrate complexes, individually have been suggestd for use as antiperspirant materials in the prior art and the combination of aluminum chloride and aluminum chlorohydrate on the one hand, and the combination of aluminum chlorohydrate and zirconyl hydroxychloride on the other hand, have also been suggested for use as an active antiperspirant, it has been unexpectedly found that combination of aluminum chloride, aluminum chlorohydrate, an aluminum zirconium polychlorohydrate complex as defined more particularly below act synergistically and at the same level of concentration of actives show a higher degree of antiperspirant activity than would be expected from the level of activity of the individual ingredients or certain combination of ingredients which are shown in the prior art. In combination with a buffering agent e.g. glycine, these materials provide a high performance antiperspirant having a low potential for skin irritation and/or fabric damage.

It is accordingly an object of the present invention to provide highly effective antiperspirant compositions.

It is also an object of this invention to provide a process for inhibiting perspiration on the skin of individuals by application to the skin area the aforesaid antiperspirant compositions.

Other and more detailed objects of this invention will be apparent from the following description and claims.

In the following description, unless otherwise specified, the percentages are expressed as percentages by weight based on the total weight of the composition.

The aluminum chloride that is incorporated in the compositions of the present invention may be aluminum chloride hydrated to various degrees. However, aluminum chloride hexahydrate ($AlCl_3.6H_2O$) has been found to be most effective and is therefore preferred for the purposes of the present invention.

The quantity of aluminum chloride that may be incorporated in the present composition may vary somewhat. Generally, the aluminum chloride will be incorporated in these compositions at a level of between about 0.5% and about 6% by weight on an anhydrous basis based on the total weight of the composition. As the hexahydrate ($AlCl_3.6H_2O$) it will be incorporated at a concentraation of from about 0.9% to about 11% by weight based on the total weight of the composition with the preferred range being from about 2% to about 6% on the same basis.

The aluminum chloride hexahydrate will usually be incorporated in the present composition as a 50% aqueous solution. When employed in this form, from about 1.8% to about 22% by weight of this composition based on the total weight of the composition will be used.

The aluminum chlorohydrate (sometimes referred to as aluminum chlorhydroxide) may also be incorporated in the composition of this invention in varying amounts. Usually, this will be used at a level in the range of from about 1% to about 15% by weight on an anhydrous basis based on the total weight of the composition with the preferred level falling in the range of from about 2% to about 10% by weight on the same weight basis. Aluminum chlorohydrate is also supplied as a 50% aqueous solution. When employed in this form, it will be used at a concentration of from 2.6% to about 38% by weight based on the total weight of the composition.

The ACH and aluminum chloride may be added to this composition in whole or in part as a powdered mixture as described in the British patent to Shin et al No. 1,347,950. This may be prepared by drying an aqueous solution of aluminum chloride hexahydrate and ACH using conventional drying techniques such as oven drying, vacuum oven drying, spray drying or freeze drying. These compositions are characterized by the fact that the molar ratio of aluminum to chloride will fall within the range of from about 0.78:1 to about 1.95:1 with the preferred range being about 1.2:1 to about 1.5:1. When the molar ratio of aluminum to chloride is less than 1, the addition of larger amounts of buffering agent e.g. glycine may be necessary to reduce irritation potential and fabric damage.

The aluminum zirconium polychlorohydrate complexes that may be incorporated in the composition of the present invention may be described by the general formula:

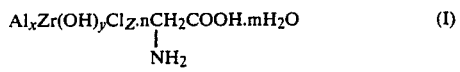

$$Al_xZr(OH)_yCl_z.nCH_2COOH.mH_2O \quad (I)$$
$$| $$
$$NH_2$$

wherein:
(a) x is a number from 2 to 10;
(b) Z is a number from 3 to 8;
(c) y equals (3x+4) −Z;
(d) the sum of y+Z is a number from 10 to 34;
(e) m is a number from 0 to 12;
(f) n is a number from 0 to 3 y ordinarily will have a value of from about 5 to about 29.

As will be clear from Formula I, the glycine may be bound in the complex or it may be absent. The presence or absence of the glycine in the complex will determine the amount of unbound glycine or other buffer that may be incorporated in the composition to increase the pH to a level of from about 2.5 to about 4.5 or the preferred pH of from about 2.8 to about 3.8.

A number of aluminum zirconium polychlorohydrate complexes are known in the prior art which are useful for the present purposes. By way of example, the following may be mentioned along with their empirical formulas: aluminum zirconium tetrachlorohydrate $(Al_4Zr(OH)_{12}Cl_4)$; aluminum zirconium tetrachlorohydrate glycine (Wickenol #E-369) $(Al_4Zr(OH)_{12}Cl_4.NH_2CH_2COOH)$; aluminum zirconium trichlorohydrate $(Al_4Zr(OH)_{13}Cl_3)$; aluminum zirconium trichlorohydrate glycine $(Al_4Zr(OH)_{13}Cl_3.NH_2CH_2COOH)$; aluminum zirconium pentachlorohydrate $(Al_{10}Zr(OH)_{29}Cl_5)$; aluminum zirconium pentachlorohydrate glycine $(Al_{10}Zr(OH)_{29}Cl_5.NH_2CH_2COOH)$; aluminum zirconium octachlorohydrate $(Al_6Zr(OH)_{14}Cl_8)$; aluminum zirconium octachlorohydrate glycine $(Al_6Zr(OH)_{14}Cl_8.NH_2CH_2COOH)$. The aluminum zirconium polychlorohydrate complex can be mixed individually with the ACH and $AlCl_3.6H_2O$ in solution or powder form or in various combinations thereof.

The OTC Panel on antiperspirants of the Food and Drug Administration has adopted certain nomenclature and specifications for various aluminum zirconium polychlorohydrates that are useful in the present invention. These are set out in Table A below:

TABLE A

| Panel Adopted Nomenclature | Metal-Halide Ratio Range | Al/Zr Ratio Range |
|---|---|---|
| Aluminum zirconium trichlorohydrate | 2.1 down to but not including 1.5:1 | 2.0 up to but not including 6.0:1 |
| Aluminum zirconium tetrachlorohydrate | 1.5 down to and including 0.9:1 | 2.0 up to but not including 6.0:1 |
| Aluminum zirconium pentachlorohydrate | 2.1 down to but not including 1.5:1 | 6.0 up to and including 10.0:1 |
| Aluminum zirconium octachlorohydrate | 1.5 down to and including 0.9:1 | 6.0 up to and including 10.0:1 |

A number of the aluminum zirconium polychlorohydrate complexes that are useful in the present invention are available commercially. Reheis Chemical Company promotes a series of materials under the general trademark REZAL TM. The following Table describes a number of these products together with their specifications:

TABLE 1

| | | |
|---|---|---|
| 1 REZAL 36G | Aluminum zirconium tetrachlorohydrex Gly (soln.) | |
| 2 REZAL 36 | Aluminum zirconium trichlorohydrate (pdr.) | |
| 3 REZAL 67 | Aluminum zirconium pentachlorohydrate (soln.) | |
| 4 REZAL 67 | Aluminum zirconium pentachlorohydrate (pdr.) | |

| | 1 | 2 | 3 | 4 |
|---|---|---|---|---|
| Approx. Al/Zr ratio | 3.6:1 | 3.6:1 | 6.7:1 | 6.7:1 |
| Approx. metal/Cl ratio | 1.4:1 | 1.6:1 | 1.7:1 | 1.7:1 |
| Concentration of solids | ~35% | 100% | ~40% | 100% |
| Aluminum(Al) | 5.0%–5.7% | 16.3%–17.7% | 7.6%–8.4% | 19.0%–21.0% |
| Zirconium(Zr) | 4.4%–5.7% | 13.8%–15.2% | 3.7%–4.3% | 9.2%–10.8% |
| Glycine | 3.6%–4.7% | — | — | — |
| Chloride(Cl) | 5.9%–6.7% | 16.0%–19.0% | 6.5%–7.2% | 16.2%–18.0% |
| Iron(Fe) | NMT 50 ppm | NMT 100 ppm | NMT 50 ppm | NMT 100 ppm |
| Heavy metals (as Pb) | NMT 10 ppm | NMT 20 ppm | NMT 10 ppm | NMT 20 ppm |
| Particle size (thru 325 mesh) | — | >97% min. | — | >97% min. |

Similar products are marketed by Wickhen Products, Inc. and the Comet Chemical Corporation.

The quantity of any aluminum zirconium polychlorohydrate complex that will be incorporated in the composition of the present invention may also vary somewhat. Usually, it will be used at a concentration level in the range of from about 5% to about 16% by weight on an anhydrous basis based on the total weight of the composition. In the preferred forms of this invention, the levels will be in the range of from about 8% to about 14% by weight on an anhydrous basis based on the total weight of the composition.

The aluminum zirconium polychlorohydrate complex of choice in the present invention is aluminum zirconium tetrachlorohydrate glycine complex. This is usually used at a level of from about 5% to about 16% by weight on an anhydrous basis based on the total weight of the composition with the preferred level being in the range of from about 8% to about 14% based on the same weight basis. The aluminum zirconium tetrachlorohydrate glycine complex is supplied as a 35% aqueous solution. When employed in this form, it is usually incorporated in the present composition at a level in the range of from about 18% to about 60% by weight based on the total weight of the composition.

Glycine, the preferred buffering agent, is an important component of the present composition. This may be incorporated as free glycine or as part of the aluminum zirconium polychlorohydrate complex or as a combination of the both. In general, the total glycine incorporated in these compositions (i.e. as free glycine, complexed glycine or a combination of both) will fall in the range of from about 0.5% to about 5% by weight based on the total weight of the composition. The preferred range of total glycine, however, is from about 1.5% to about 3% on the same weight basis.

Other buffering or complexing agents besides glycine can also be used in this invention. For example, other amino acids or their salts (e.g. sodium glycinate, dihydroxy aluminum glycinate), urea, organic base containing nitrogen, metal hydroxide, carbonate, and oxide including alkaline and alkaline earth metal ($Mg(OH)_2$, $Na_2CO_3$, ZnO, etc.). These buffering agents can be used alone or in combination with glycine to give the composition a pH in the range of from 2.5 to 4.5 (preferably 2.8 to 3.8).

These complexing and buffering agents serve to reduce irritation potential and fabric damage. They also function to stabilize the antiperspirant system.

The compositions of the present invention may take a variety of dosage forms. Thus, they might be emulsion roll-on products or a clear hydro-alcoholic or aqueous roll-on products. Aqueous solutions of the aluminum chloride, ACH, aluminum zirconium polychlorohydrate complex and buffering agent e.g. glycine may be spray dried into an impalpable powder. This can be used as such or incorporated into sticks, suspensions, powders or roll-on products.

Although the compositions of the present invention may take a variety of forms, they appear very effective in system that contain a relatively high water content. These may take the form of solution or emulsion in which the active ingredients (i.e. the aluminum chloride, ACH, aluminum zirconium polychlorohydrate complex and buffer) are contained in the aqueous phase. The aqueous emulsion systems are preferred since they give more organoleptically elegant compositions. These emulsion systems will usually be of the oil-in-water type in which the active ingredients will be contained in the continuous aqueous phase.

The quantity of water that may be contained in these compositions may vary somewhat. Usually, it will comprise from about 40% to about 80% by weight based on the total weight of the composition, the preferred range being from about 60% to about 75% on the same weight basis.

The emulsion type products of the present invention may also contain other ingredients that are commonly found in roll-on antiperspirant of the lotion or emulsion type. These will include such things as emollients, surfactants, sequestering agents, perfumes, coloring agents, etc. By way of illustrating the emollients that may be employed herein, mention may be made of fatty acid esters (isopropyl myristate, isopropyl palmitate); diesters of dicarboxylic acids (diisopropyl adipate), polyoxyalkylene glycol esters (polypropylene glycol 2000 monooleate); propylene glycol diesters of short chain fatty acids ($C_8$–$C_{10}$) (Neobee M-20); polyoxypropylene fatty ethers (Procetyl, Arlamol E, Witconol APS, Witconol APM, etc.), propoxylated monohydric alcohol M.W. 880-930 (Fluid AP), fatty alcohol (hexadecyl alcohol), silicone oils (dimethyl polysiloxane, 10–2000 centistokes), cyclomethicones (volatile silicone 7207 and 7158-Union Carbide), polyoxyethylene polyoxypropylene fatty ether (Procetyl AWS Modified, Witconol APES). Alone or mixtures of the above non-polar liquids are equally suitable for the purposes of this invention. Generally, the above emollients are organic oily liquids which are non-polar in character and have (a) a boiling point under atmospheric pressure not lower than about 120° C.; (b) a specific gravity between about 0.7 and 1.6, preferably between 0.7 and 1.2.

The quantity of emollient employed will vary somewhat, the level usually being within the range of from about 1% to about 30% by weight based on the total weight of the composition. Preferably, this will fall in the range of from about 2% to about 15% on the same weight basis.

A variety of surfactants and combinations of surfactants are also useful in preparing the present lotion or emulsion type products. These include such materials as generally nonionic, cationic and amphoteric surfactants which can be used in antiperspirant emulsion systems. Examples are as follows:

I. Nonionic Surfactants
1. Polyoxyethylene fatty ethers—Brij 30, Brij 35, Brij 72, Brij 78, etc.
2. Polyoxypropylene polyoxyethylene fatty ethers—Procetyl AWS, Witconol APEM, Witconol APES, etc.
3. Polyoxyethylene alkyl phenyl ethers—Igepal CO 530, etc.
4. Polyoxyethylene sorbitan fatty acid esters—Tween 20, Tween 80, etc.
5. Sorbitan fatty acid esters—Span 60, Span 85, etc.
6. Lanolin ethers—Laneto 50, Solulan 98, etc.
7. Fatty alcohols and polyoxyethylene fatty ethers—Promulgen G, Polawax, etc.

II. Cationic Surfactants
N(Lauryl colamino formyl methyl)pyridinium chloride (Emcol E607L)

III. Amphoteric Surfactants
Coconut imidazoline (Monateric CA-35%)

IV. Auxiliary Surfactants
1. Glyceryl fatty acid esters—Glyceryl monostearate
2. Fatty acid amides—Witcamide 70 (Witco Chem. Co.)
3. Fatty alcohols—Stearyl alcohol As in the case with the emollients, the quantity employed can vary somewhat. For the most part, this will be in the range of from about 1% to about 10% by weight on an anhydrous basis based on the total weight of the composition with the preferred range being from about 2% to about 6% on the same weight basis.

As indicated above, one of the popular antiperspirant systems employed in the prior art is an aluminum zirconium trichlorohydrate glycine complex. The present system has the following advantages over said popular system:

1. Low cost of goods. The above popular system is much more expensive than either $AlCl_3.6H_2O$ or ACH.
2. Better emulsion stability and more ease to manufacture. Straight Al/Zr polychlorohydrate glycine systems are difficult to stabilize and to manufacture as emulsions.

3. Low fabric staining potential. Generally, straight Al/Zr polychlorohydrate glycine salts stain more than aluminum salts.

The following Examples are given to further illustrate the present invention. It is to be understood, however, that the invention is not limited thereto.

EXAMPLE 1

Formula 1908

| Ingredients | % by Wt. | |
|---|---|---|
| PPG-11 stearyl ether | 2.25 | |
| Polyoxyethylene(2)stearyl ether | 1.65 | |
| Polyoxyethylene(20)stearyl ether | 0.60 | |
| Perfume | 0.30 | |
| Disodium edetate, dihydrate | 0.10 | |
| Water, deionized | 35.40 | |
| Aluminum chlorhydroxide, 50% | 18.00 | (Anhydr. 7.2%) |
| Aluminum chloride hexahydrate solution, 50% | 6.00 | (Anhydr. 1.7%) |
| Aminoacetic acid (Glycine Crystal USP) | 0.50 | |
| Aluminum zirconium tetrachlorohydrex-glycine solution, 35% | 35.00 | (Anhydr. 9.1%) |
| Color FD&C Blue #1 (0.1% Aq. Sol.) | 0.20 | |
| | 100.00 | |

Appearance: Smooth, opaque lotion
Color: Pale blue
pH: 3.3 ± 0.3
Viscosity: #3 spindle at 20 RPM 15 seconds
Overnight viscosity: 500–1500 cps Procedure:
1. In a suitable stainless steel kettle, melt together polyoxypropylene fatty alcohol ethers, polyoxyethylene(2)stearyl ether and polyoxyethylene(20)stearyl ether by heating to 140° F. Add the perfume and mix together just prior to Step 3.
2. In a separate stainless steel kettle, dissolve the disodium edetate in the water and heat to 140° F.
3. Slowly add the oil phase to the water phase (both at 140° F.) using a Lightnin' mixer at slow agitation. Maintain the temperature of 140° F. for 15 minutes.
4. At 140° F., slowly add to the batch, using slow agitation, a solution consisting of the aluminum chlorhydroxide, aluminum chloride hexahydrate, glycine and aluminum zirconium tetrachlorohydrex-glycine solution which has been preheated to 120° F. Continue agitation and cool the batch to 125° F. Mix for 15 minutes, maintaining the batch temperature at 120° F.–125° F.
5. Cool the batch to 105° F., add the dye solution and continue agitation and cooling.
6. When the batch temperature reaches 80°–85° F., stop agitation and adjust for water loss, if necessary.

EXAMPLE 2

The composition and procedure of Example 1 is followed except that in place of the PPG-11 stearyl ether, Arlamol ESP (PPG-15 stearyl ether) is employed.

EXAMPLE 3

Formula 1956

Following the procedure of Example 1, the following composition is prepared:

| Ingredients | % by Wt. |
|---|---|
| PPG-11 stearyl ether | 2.25 |
| Polyoxyethylene(2)stearyl ether | 1.65 |
| Polyoxyethylene(20)stearyl ether | 0.60 |
| Perfume | 0.32 |
| Disodium edetate, dihydrate | 0.10 |
| Water, deionized | 35.13 |
| Butylated hydroxytoluene | 0.05 |
| Aluminum chlorhydroxide, 50% | 18.00 |
| Aluminum chloride hexahydrate solution, 50% | 6.00 |
| Aminoacetic acid (Glycine Crystal USP) | 0.50 |
| Aluminum zirconium tetrachlorohydrex-glycine solution, 35% | 35.00 |
| D&C Red #19 (0.1% Aq. Sol.) | 0.08 |
| D&C Yellow #10 (0.1% Aq. Sol.) | 0.32 |
| | 100.00 |

Appearance: Smooth, opaque lotion
Color: Pink
pH: 3.3 ± 0.3
Viscosity: #3 spindle at 20 RPM 15 seconds
Overnight viscosity: 500–1500 cps

EXAMPLE 4

The composition and procedure of Example 3 is followed excepting that in place of the PPG-11 stearyl ether, Arlamol ESP (PPG-15 Stearyl Ether) is used.

EXAMPLE 5

The procedure of Example 1 is followed and the following composition is prepared:

| Ingredients | % by Wt. |
|---|---|
| PPG-11 stearyl ether | 2.25 |
| Polyoxyethylene(2)stearyl ether | 1.65 |
| Polyoxyethylene(20)stearyl ether | 0.60 |
| Perfume | 0.30 |
| Disodium edetate, dihydrate | 0.10 |
| Water, deionized | 31.40 |
| Aluminum chlorhydroxide, 50% | 12.00 |
| Aluminum chloride hexahydrate solution, 50% | 6.00 |
| Aminoacetic acid (Glycine Crystal USP) | 0.50 |
| Aluminum zirconium tetrachlorohydrex-glycine solution, 35% | 45.00 |
| FD&C Blue #1 (0.1% Aq. Sol.) | 0.20 |
| | 100.00 |

Appearance: Smooth, opaque lotion
Color: Pale blue
pH: 3.3 ± 0.3
Viscosity: #3 spindle at 20 RPM 15 seconds
Overnight viscosity: 500–1500 cps

EXAMPLE 6

The procedure and composition of Example 5 is followed excepting that in place of the PPG-11 stearyl ether, Arlamol ESP (PPG-15 Stearyl Ether) is employed.

EXAMPLE 7

Formula 1979

The procedure of Example 1 is followed and the following composition is prepared:

| Ingredients | % by Wt. |
|---|---|
| PPG-11 stearyl ether | 2.25 |
| Polyoxyethylene(2)stearyl ether | 1.65 |
| Polyoxyethylene(20)stearyl ether | 0.60 |
| Perfume | 0.30 |
| Disodium edetate, dihydrate | 0.10 |
| Water, deionized | 35.40 |
| Aluminum chlorhydroxide, 50% | 15.50 |
| Aluminum chloride hexahydrate solution, 50% | 8.00 |
| Aminoacetic acid (Glycine Crystal USP) | 1.00 |
| Aluminum zirconium tetrachlorohydrex-glycine solution, 35% | 35.00 |
| FD&C Blue #1 (0.1% Aq. Sol.) | 0.20 |
| | 100.00 |

Appearance: Smooth, opaque lotion
Color: Pale blue
pH: 3.3 ± 0.3
Viscosity: #3 spindle at 20 RPM 15 seconds
Overnight viscosity: 500-2000 cps

EXAMPLE 8

The composition and procedure of Example 7 is followed excepting that in place of the PPG-11 stearyl ether, Arlamol ESP (PPG-15 Stearyl Alcohol) is employed.

EXAMPLE 9

Formula 1991

The procedure of Example 1 is followed and the following composition is prepared:

| Ingredients | % by Wt. | |
|---|---|---|
| PPG-11 stearyl ether | 2.25 | |
| Polyoxyethylene(2)stearyl ether | 1.65 | |
| Polyoxyethylene(20)stearyl ether | 0.60 | |
| Perfume | 0.30 | |
| Disodium edetate, dihydrate | 0.10 | |
| Water, deionized | 31.40 | |
| Aluminum chlorhydroxide, 50% | 10.00 | (Anhydr. 4%) |
| Aluminum chloride hexahydrate solution, 50% | 8.00 | (Anhydr. 2.2%) |
| Aminoacetic acid (Glycine Crystal USP) | 0.50 | |
| Aluminum zirconium tetrachlorohydrex-glycine solution, 35% | 45.00 | (Anhydr. 11.75%) |
| FD&C Blue #1 (0.1% Aq. Sol.) | 0.20 | |
| | 100.00 | |

Appearance: Smooth, opaque lotion
Color: Pale blue
pH: 3.3 ± 0.3
Viscosity: #3 spindle at 20 RPM 15 seconds
Overnight viscosity: 500-1500 cps

EXAMPLE 10

The composition and procedure of Example 9 is followed excepting that in place of the PPG-11 stearyl ether, Arlamol ESP (PPG-15 Stearyl Ether) is employed.

EXAMPLE 11

Formula 1955

The procedure of Example 1 is followed and the following composition is prepared:

| Ingredients | % by Wt. |
|---|---|
| PPG-11 stearyl ether | 2.25 |
| Polyoxyethylene(2)stearyl ether | 1.65 |
| Polyoxyethylene(20)stearyl ether | 0.60 |
| Perfume | 0.30 |
| Disodium edetate, dihydrate | 0.10 |
| Water, deionized | 35.60 |
| Aluminum chlorhydroxide, 50% | 18.00 |
| Aluminum chloride hexahydrate solution, 50% | 6.00 |
| Aminoacetic acid (Glycine Crystal USP) | 0.50 |
| Aluminum zirconium tetrachlorohydrex-glycine solution, 35% | 35.00 |
| | 100.00 |

Appearance: Smooth, opaque lotion
Color: White
pH: 3.3 ± 0.3
Viscosity: #3 spindle at 20 RPM 15 seconds
Overnight viscosity: 500-1500 cps

EXAMPLE 12

The composition and procedure of Example 11 is followed excepting that in place of the PPG-11 stearyl ether, Arlamol ESP (PPG-15 Stearyl Ether) is employed.

EXAMPLE 13

Formula BA 1810-64

Aluminum zirconium trichlorohydrate 31 powder was employed. The number following the term "trichlorohydrate" in this and other Examples designates the Al/Zr molar ratio in the compound. Thus, for example, 31 designates an Al/Zr molar ratio of 3/1.

| | % by Wt. |
|---|---|
| Primary Emulsion A | |
| PPG-11 stearyl ether | 5.56 |
| Polyoxyethylene(2)stearyl ether | 4.07 |
| Polyoxyethylene(20)stearyl ether | 1.48 |
| Perfume | 0.74 |
| Disodium edetate, dihydrate | 0.25 |
| FD&C Blue #1 (0.1% Aq. Sol.) | 0.49 |
| Water, deionized | 87.41 |
| | 100.00 |
| Ingredients | |
| Al/Zr trichlorohydrate 31 powder | 10.00 |
| ACH 50% solution | 18.00 |
| AlCl$_3$.6H$_2$O, 50% solution | 6.00 |
| Glycine | 1.50 |
| Water, deionized | 24.00 |
| Primary Emulsion A q.s. to | 100.00 | pH: 3.4 ± 0.3
Overnight viscosity: 500-1500 cps

EXAMPLE 14

Formula BA 1810-65

Aluminum zirconium trichlorohydrate 21 powder (Al/Zr molar ratio=2/1) was used:

| Ingredients | % by Wt. |
|---|---|
| Al/Zr trichlorohydrate 21 powder | 10.00 |
| ACH 50% solution | 18.00 |
| AlCl$_3$.6H$_2$O, 50% solution | 6.00 |
| Glycine | 1.50 |
| Water, deionized | 24.00 |
| Primary Emulsion A q.s. to | 100.00 | pH: 3.5 ± 0.3

-continued

| Ingredients | % by Wt. |
|---|---|
| Overnight viscosity: 500–1500 cps | |

EXAMPLE 15

Formula BA 1810-56

Aluminum zirconium octachlorohydrex-glycine powder 81 (Al/Zr molar ratio=8/1) was used:

| Ingredients | % by Wt. |
|---|---|
| Al/Zr octachlorohydrex-glycine powder 81 | 15.00 |
| ACH 50% solution | 10.00 |
| AlCl$_3$.6H$_2$O solution | 8.00 |
| Glycine | 0.50 |
| Water, deionized | 26.00 |
| Primary Emulsion A q.s. to | 100.00 |
| pH: 3.2 ± 0.3 | |
| Overnight viscosity: 500–1500 cps | |

EXAMPLE 16

Formula BA 1810-57

Aluminum zirconium pentachlorohydrate solution (Al/Zr molar ratio=10/1) was used:

| Ingredients | % by Wt. |
|---|---|
| Al/Zr pentachlorohydrate solution, 30% | 35.00 |
| ACH 50% solution | 10.00 |
| AlCl$_3$.6H$_2$O 50% solution | 8.00 |
| Glycine | 2.00 |
| Water, deionized | 4.50 |
| Primary Emulsion A q.s. to | 100.00 |
| pH: 3.4 ± 0.3 | |
| Overnight viscosity: 450–1500 cps | |

EXAMPLE 17

Formula BQ 1856-83

Different buffering agent such as sodium carbonate is used as an additional buffering agent in this Example.

| | % by Wt. |
|---|---|
| Primary Emulsion B | |
| PPG-11 stearyl ether | 6.43 |
| Polyoxyethylene(2)stearyl ether | 4.71 |
| Polyoxyethylene(20)stearyl ether | 1.71 |
| Perfume | 0.86 |
| Disodium edetate, dihydrate | 0.29 |
| FD & C Blue #1 (0.1% aq. sol.) | 0.57 |
| Water, deionized | 85.43 |
| | 100.00 |
| Ingredients | |

| | % by Wt. |
|---|---|
| Al/Zr tetrachlorohydrex-glycine solution, 35% | 45.00 |
| ACH, 50% solution | 10.00 |
| AlCl$_3$.6H$_2$O, 50% solution | 8.00 |
| Glycine | 1.20 |
| Sodium carbonate monohydrate | 0.50 |
| Water, deionized | 0.30 |
| Primary Emulsion B q.s. to | 100.00 |
| pH: 3.4 ± 0.3 | |
| Overnight viscosity: 500–1500 cps | |

EXAMPLE 18

Formula BQ 1856-83

Magnesium hydroxide was used as an additional buffering agent.

| Ingredients | % by Wt. |
|---|---|
| Al/Zr tetrachlorohydrex-glycine solution, 35% | 45.00 |
| ACH, 50% solution | 10.00 |
| AlCl$_3$.6H$_2$O, 50% solution | 8.00 |
| Glycine | 0.50 |
| Magnesium hydroxide | 0.50 |
| Water, deionized | 1.00 |
| Primary Emulsion B q.s. to | 100.00 |
| pH: 3.4 ± 0.3 | |
| Overnight viscosity: 500–1500 cps | |

EXAMPLE 19

Formula 1509-61

| Ingredients | % by Wt. |
|---|---|
| PPG-11 stearyl ether | 2.25 |
| Polyoxyethylene(2)stearyl ether | 1.65 |
| Polyoxyethylene(20)stearyl ether | 0.60 |
| Perfume | 0.30 |
| Water, deionized | 41.20 |
| Disodium edetate, dihydrate | 0.10 |
| DC Antifoam AF, 25% | 0.10 |
| Al/Zr tetrachlorohydrex-glycine solution, 35% | 35.00 |
| ACH, 50% solution | 15.00 |
| AlCl$_3$.6H$_2$O, 50% solution | 3.00 |
| Glycine | 0.60 |
| FD & C Blue #1 (0.1% aq. sol.) | 0.20 |
| | 100.00 |
| pH: 3.4 ± 0.3 | |
| overnight viscosity: 400–1200 cps | |

To demonstrate that the combination of aluminum chloride, ACH, aluminum zirconium polychlorohydrate and glycine act synergistically, a number of formulas identified in Table II below were prepared. Formula #1908 is representative of the present invention.

TABLE II

| Ingredients | % by Wt. based on Total Weight | | | | Commercial Emulsion Roll-On (BR-4504) |
|---|---|---|---|---|---|
| | F #1052 | F #1676 | F #1908 | F #1341 | |
| ACH (% anhydrous basis) | 18.3 | — | 7.2 | 16.2 | — |
| AlCl$_3$.6H$_2$O (% anhydrous basis) | — | — | 1.7 | 2.0 | — |
| Al/Zr tetrachlorohydrate (% anhydrous basis) | — | 18.6 | 9.1 | — | Al/Zr trichlorohydrate (% anhy. basis) 19.7 |
| Glycine | — | 2.8 | 1.9 | 2.0 | Glycine 4.2 |
| PPG-11 stearyl | 3.0 | 2.0 | 2.25 | 3.5 | — |

TABLE II-continued

| Ingredients | % by Wt. based on Total Weight | | | | Commercial Emulsion Roll-On (BR-4504) |
|---|---|---|---|---|---|
| | F #1052 | F #1676 | F #1908 | F #1341 | |
| ether | | | | | |
| Polyoxyethylene(2) stearyl ether | 1.9 | 1.5 | 1.65 | 2.3 | PEG-40 stearate, Glyceryl stearate, Glycerin, |
| Polyoxyethylene(20) stearyl ether | 1.1 | 0.6 | 0.6 | 1.2 | Refined paraffin, Isopropyl palmitate, Mg/Al silicate and Fragrance |
| Disodium edetate, dihydrate | 0 | 0.1 | 0.1 | 0.1 | |
| Perfume & Color Water q.s. to 100 } | ⎯⎯⎯⎯⎯⎯⎯⎯⎯⎯⎯⎯⎯⟶ | | | | |
| Total Actives | 18.3 | 18.6 | 18.5 | 18.2 | 19.7 Total actives |
| Total Glycine | 0 | 2.8 | 1.9 | 2.0 | 4.2 Total Glycine |

As will be noted, each of these formulas is similar excepting for the active ingredients that are employed. Further, each contains the total active ingredients at essentially the same concentration i.e. about 18% on an anhydrous basis.

Each of these compositions was tested for antiperspirant activity. The general procedure employed was as described in Federal Register, Vol. 43, Number 196, Oct. 10, 1978. It is called the gravimetric axillary antiperspirant test. Paired comparison (treated vs. treated) studies of the antiperspirant effectiveness of antiperspirant emulsion.

The details of the test procedure are given below.

Test Procedure

A random test pattern supplied by Statistical Services is employed, e.g. if one test material is evaluated, half of the panelists receives the test material under the left axilla while the remaining half receives it under the right. The opposite axilla serves as a control. If two test materials are evaluated, half the panel has product A applied to the left axilla and product B to the right while the remaining panelists have the reverse product/axilla allocations.

The test is conducted during a five-day period (Monday through Friday). Sweating is induced under environmental conditions of 100° F.±2° and 40% relative humidity ±2%.

Day 1

Control measurement followed by product application

Panelists wait one-half hour at room temperature (approximately 65°-80° F.) after which time they enter the tet room. They then place the untared Webril Pads (which are folded in half to a size of 4"×2") in their axillae. Subjects sit in the test room for a 40 minute warm-up period. At the end of this period, the warm-up pads are removed by the panelists and are discarded.

The panelists remove the plastic bags containing the tared collection pads from the manila envelopes. The subjects insert the pads as directed by a technician. The pads remain in the axilla for a period of 20 minutes. After such time, the panelists are instructed to remove the pads and to place them into the designated plastic bags which are then returned to the manila envelopes.

The panelists exit the test room, hand in their envelopes, and then wash their axillae with tepid water with the aid of gauze pads and towel dry them. Approximately one to three minutes later, the test material is applied and the panelists leave. The plastic bags are removed from the manila envelopes and are weighed by a technician. Panelists must perspire at least 200 mg/axilla to continue participation on the panel.

Day 2

Product application only

Panelists wait one-half hour at room temperature, after which time they wash their axillae with tepid water with the aid of gauze pads and towel dry them. Approximately one to three minutes later, the test material is applied and the panelists leave.

Day 3

Product application and collection

Panelists wait one-half hour at room temperature, after which time they wash their axillae as described above. Approximately one to five minutes later the test material is applied. The panelists then wait one hour at room temperature. Then they enter the test room for a 40-minute warm-up and place the untared pads in their axillae. At the end of this period, the warm-up pads are removed and discarded.

The panelists remove the plastic bags containing the tared collection pads from the manila envelopes. They insert the pads as directed by a technician. The pads remain in the axillae for a period of 20 minutes. Then the panelists are instructed to remove the pads and to place them into the designated plastic bags which are then returned to the manila envelopes. The panelists exit the test room, hand in their envelopes, and leave. The plastic bags are removed from the manila envelopes and are weighed by a technician.

Day 4

Product application only

Same as Day 2.

Day 5

Product application and collection

Same as Day 3.

The results of the test are summarized as follows:

I.

Formula #1908 vs. Formula #1052

Results:

The data from this study, employing 47 female subjects, were submitted to the Statistical Services Department for evaluation.

Briefly, their analysis indicated that Antiperspirant Roll-on Formula #1908 was significantly more effective than Formula #1052 at the 0.01 level.

This conclusion is supported by the A/B ratio (amount of sweat collected from A treated axilla over B treated axilla) for the final treatment-collection day (adjusted by control) averaging 0.819 which is significantly different from 1.0 equality.

The above data indicates that Formula #1908 is about 18% more effective than Formula #1052.

II.

Formula #1908 vs. Formula #1676

Results:

The data from this study, employing 46 female subjects, were submitted to the Statistical Services Department for evaluation.

Briefly, their analysis indicated that Formula #1908 was significantly more effective than Formula #1676 at the 0.01 level.

This conclusion is supported by the A/B ratio for the final treatment-collection day (adjusted for control) averaging 0.883 which is significantly different from 1.0 equality.

The above data indicates that Formula #1908 is about 12% more effective than Formula #1676.

III.

Formula #1908 vs. Commercial Emulsion Roll-On Formula #BR 4504

Results:

The data from this study, employing 48 female subjects, were submitted to the Statistical Services Department for evaluation.

Briefly, their analysis indicates that Formula #1908 was significantly more effective than Commercial Emulsion Roll-On at the 0.01 level.

This conclusion is supported by the A/B ratio for the final treatment-collection day (adjusted for control) averaging 0.881 which is significantly different from 1.0 equality.

The above data indicates that Formula #1908 is about 12% more effective than Formula #BR 4504.

IV.

Formula #1341 (see Table II) which contains as antiperspirant actives a combination of ACH and $AlCl_3.6H_2O$ (at a level of about 18.2) in a similar manner was shown to be on the average 9.6% less effective than the Commercial Emulsion Roll-on (BR 4504) which contains 19.7% Al/Zr trichlorohydrate as the antiperspirant active (see Table II). The latter, however, has also been shown to be less effective than Formula #1908 embodied in the present invention i.e. Formula #1908 was about 12% more effective than Formula #BR 4505 (see Paragraph III).

V.

Formula #1991 (See Example 9) in a similar manner was shown to be 15% more effective than a commercial suspension roll-on product identified as Formula #BR 4751. The latter has the following composition:

| Formula # BR 4751 | |
|---|---|
| Ingredients | % by Wt. |
| Aluminum zirconium tetrachloro- | 13.8 |

| Formula # BR 4751 | |
|---|---|
| Ingredients | % by Wt. |
| hydrate (anhydrous basis) | |
| Glycine | 2.0 |
| Bentone 38 | 3.25 |
| Cyclomethicone and Perfume q.s. to | 100.00 |

Although the invention has been described with reference to specific forms thereof, it will be understood that many changes and modifications may be made without departing from the spirit of this invention.

What is claimed is:

1. An antiperspirant composition buffered to a pH in the range of from about 2.5 to about 4.5, said composition containing as active ingredients, on an anhydrous basis:
    (1) from about 1.5% to about 3.3% aluminum chloride,
    (2) from about 2% to about 10% aluminum chlorohydrate,
    (3) from about 8% to about 14% of an aluminum zirconium polychlorohydrate complex, and
    (4) from about 1.5% to about 3% glycine, the balance of the composition containing a suitable quantity of at least one carrier, all percentages being weight percentages based on total anhydrous composition weight.

2. The composition of claim 1 containing about 1.7% aluminum chloride, about 7.2% aluminum chlorohydrate, about 9.1% aluminum zirconium tetrachlorohydrate-glycine, and about 0.50% glycine.

3. The composition of claim 2 wherein the carrier is aqueous and the composition also contains about 2.25% polypropylene glycol(11)stearyl ether, about 1.65% polyoxyethylene(2)stearyl ether and about 0.6% polyoxyethylene(20)stearyl ether.

4. The composition of claim 3 which also contains about 0.1% disodium edetate dihydrate.

5. The composition of any one of claim 1-4 in the form of an emulsion comprising a water phase wherein the active ingredients are in said water phase.

6. The composition of claim 1 containing about 2.2% aluminum chloride, about 4.0% aluminum chlorohydrate, about 11.75% aluminum zirconium tetrachlorohydrate-glycine and about 0.50% glycine.

7. The composition of claim 6 wherein the carrier is an aqueous carrier and the composition also contains about 2.25% polypropylene glycol(11)stearyl ether, about 1.65% polyoxyethylene(2)stearyl ether.

8. The composition of claim 7 which also contains about 0.1% disodium edetate dihydrate.

9. The composition of any of claims 6 through 8 in the form of an emulsion comprising a water phase, wherein the active ingredients are in said water phase.

10. An antiperspirant composition buffered to a pH in the range of from about 2.8 to about 3.8, said composition containing as active ingredients, on an anhydrous basis:
    (1) from about 1.7% to about 2.2% aluminum chloride,
    (2) from about 4% to about 7.2% aluminum chlorohydrate,
    (3) from about 9.1% to about 11.75% of an aluminum zirconium polychlorohydrate complex, and (4) about 1.5 to about 3% glycine, the balance of the composition containing a suitable quantity of at least one carrier, all percentages being weight percentages based on total anhydrous composition weight.

11. The composition of claims 1 or 9 wherein the aluminum zirconium polychlorohydrate complex is selected from the group consisting of:
aluminum zirconium tetrachlorohyrate;
aluminum zirconium tetrachlorohydrate glycine;
aluminum zirconium trichlorohydrate;
aluminum zirconium trichlorohydrate glycine;
aluminum zirconium pentachlorohydrate;
aluminum zirconium pentachlorohydrate glycine;
aluminum zirconium octachlorohydrate;
aluminum zirconium octachlorohydrate glycine;
and mixtures thereof.

12. A method of inhibiting perspiration in a subject which comprises applying to the skin of said subject an effective amount of the composition of any one of claims 1-11.

* * * * *

UNITED STATES PATENT AND TRADEMARK OFFICE
CERTIFICATE OF CORRECTION

PATENT NO. : 4,774,079
DATED : September 27, 1988
INVENTOR(S) : C. T. Shin, M. S. Slade, A. Nersesian It is certified that error appears in the above-identified patent and that said Letters Patent is hereby corrected as shown below:

On the cover page of the patent, in the first column, at item [63], line 1, immediately after "Ser. No.", the number reading "464,268" should read --464,278--.

At column 1, line 9, immediately after "No.", the number "464,268" should read --464,278--.

Signed and Sealed this
Fourteenth Day of November, 1989

*Attest:*

JEFFREY M. SAMUELS

*Attesting Officer*     *Acting Commissioner of Patents and Trademarks*